US009288614B1

(12) United States Patent
Young et al.

(10) Patent No.: US 9,288,614 B1
(45) Date of Patent: Mar. 15, 2016

(54) SYSTEMS AND METHODS FOR INITIATING A COMMUNICATION LINK BETWEEN AN IMPLANTABLE MEDICAL DEVICE AND AN EXTERNAL DEVICE

(71) Applicant: Pacesetter, Inc., Sunnyvale, CA (US)

(72) Inventors: Chao-Wen Young, Cupertino, CA (US); Yongjian Wu, Saratoga, CA (US); Mostafa Sadeghi, Los Angeles, CA (US); Erik Shreve, Dallas, TX (US); Andrew Rissing, Allen, TX (US); Jun Yang, Valencia, CA (US); Heidi Hellman, Los Angeles, CA (US); Katie Hoberman, Winnetka, CA (US); Samir Shah, Valencia, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 14/637,156

(22) Filed: Mar. 3, 2015

(51) Int. Cl.
*A61N 1/00* (2006.01)
*H04W 4/00* (2009.01)
*A61N 1/372* (2006.01)
*H04W 76/02* (2009.01)
*H04B 1/3827* (2015.01)
*H04B 1/00* (2006.01)

(52) U.S. Cl.
CPC ........... *H04W 4/008* (2013.01); *A61N 1/37223* (2013.01); *H04B 1/385* (2013.01); *H04W 76/023* (2013.01)

(58) Field of Classification Search
CPC ............................. A61N 1/08; A61N 1/37252
USPC ............................................ 607/60; 455/41.2
See application file for complete search history.

(56) References Cited

U.S. PATENT DOCUMENTS

2004/0260363 A1* 12/2004 Arx ..................... A61N 1/37252
607/60
2006/0025834 A1* 2/2006 Von Arx ................... A61N 1/08
607/60

* cited by examiner

*Primary Examiner* — Lee Nguyen
(74) *Attorney, Agent, or Firm* — Theresa A. Raymer

(57) ABSTRACT

Systems and methods are provided for initiating a bi-directional communication link with an implantable medical device. The systems and methods configure an implantable medical device (IMD) to detect activation fields from a triggering device when the triggering device is positioned proximate to the IMD, and to identify a field characterization of the activation field. The systems and methods further configure the IMD to establish a bi-directional communication link with an external device through a select communication initialization mode form a plurality of communication initialization modes defined by a wireless protocol in response to the field characterization of the activation field.

20 Claims, 8 Drawing Sheets

US 9,288,614 B1

SYSTEMS AND METHODS FOR INITIATING A COMMUNICATION LINK BETWEEN AN IMPLANTABLE MEDICAL DEVICE AND AN EXTERNAL DEVICE

BACKGROUND OF THE INVENTION

Embodiments of the present disclosure generally relate to systems and methods for initiating a bi-directional communication link between devices, and more particularly to initiating a communication link between implantable medical devices and external devices with a triggering device.

An implantable medical device ("IMD") is a medical device that is configured to be implanted within a patient anatomy and commonly employ one or more leads with electrodes that either receive or deliver voltage, current or other electromagnetic pulses (generally "energy") from or to an organ or tissue for diagnostic or therapeutic purposes. In general, IMDs include a battery, electronic circuitry, such as a pulse generator and/or a microprocessor that is configured to handle RF communication with an external device as well as control patient therapy. The components of the IMD are hermetically sealed within a metal housing (generally referred to as the "can").

IMDs are programmed by and transmit data to external devices controlled by physicians and/or the patient. The external devices communicate by forming wireless bi-directional communication links with the IMDs. Restrictions may be placed on which external device may form a wireless bi-directional communication link with the IMD. For example, an external device of the patient (e.g., patient's programmer) may only be configured to form a wireless bi-directional communication link with the IMD implanted in the patient. However, the external device of the clinician (e.g., doctor, nurse) may be configured to form wireless bi-directional communication links with multiple IMDs.

Recently, these external devices may communicate using commercial protocols compatible with commercial wireless devices such as tablet computers, smartphones, and the like. However, commercial protocols have limited pairing procedures for establishing secure communication links. For example, commercial protocols can allow external devices to establish communication links at ranges of ten meters or more. The range of the commercial protocols enable external devices to form communication links in a different location (e.g., room) than the IMD and not in view of the patient. Thereby, allowing external devices to communicate with the IMD that are not known and/or authorized by the patient. A need exists for improved methods and systems that establish a communication link with an IMD using a commercial protocol.

BRIEF SUMMARY

In accordance with an embodiment herein, a method is provided for initiating a bi-directional communication link. The method may include configuring an implantable medical device (IMD) to detect an activation field from a triggering device when the triggering device is positioned proximate to the IMD, and to identify a field characterization of the activation field. The method may also include configuring the IMD to establish a bi-directional communication link with an external device to a select communication initialization mode from a plurality of communication initialization modes defined by a wireless protocol in response to the field characterization of the activation field.

In an embodiment, a system is provided for initiating a bi-directional communication link. The system may include an external device, a triggering device, and an implantable medical device (IMD). The IMD may comprise a trigger circuit. The trigger circuit is configured to detect an activation field from the triggering device when the triggering device is positioned proximate to the IMD. The IMD further may be configured to identify a field characterization of the activation field and establish a bi-directional communication link with an external device through a select communication initialization mode from a plurality of communication initialization modes defined by a wireless protocol in response to the field characterization of the activation field.

DETAILED DESCRIPTION

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Various embodiments described herein include a method and/or system to provide a pairing and/or bonding procedure between two devices using a triggering device. The triggering device (e.g., a magnet, an inductive communication circuit, a near field communication circuit, an electric motor) may emit or transmit an activation field, which may be detected by an implantable medical device (IMD). When the activation field is detected by the IMD, the IMD may enter or transition into a communication initialization mode corresponding to the pairing and/or bonding procedure. The pairing and/or bonding procedure may be defined by a wireless protocol (e.g., Bluetooth, Bluetooth low energy, ZigBee). The pairing and/or bonding procedure may include exchanging information to generate passkeys in both the IMD and an external device to establish a communication link. A technical effect of various embodiment described herein strengthen pairing and/or bonding procedures for wireless protocols by providing proximity detection based on the triggering device and the activation field for the pairing and/or bonding procedure of available wireless protocols. A technical effect of positioning the triggering device proximate to the IMD, thereby the patient, is awareness of the patient and proximity protection against the IMD 101 initiating a communication link from an untrusted or unauthorized external device.

Figure 1:
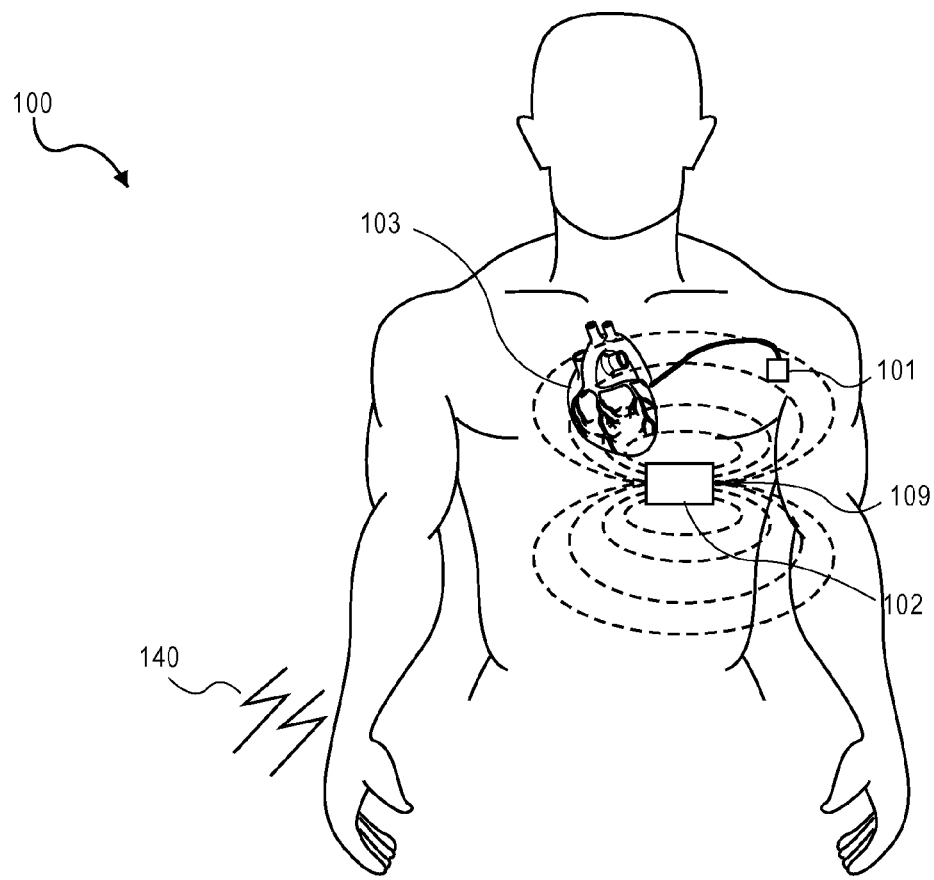
FIG. 1 illustrates simplified block diagram of a system for initiating a bi-directional communication link, according to an embodiment of the present disclosure.
Figure 1:
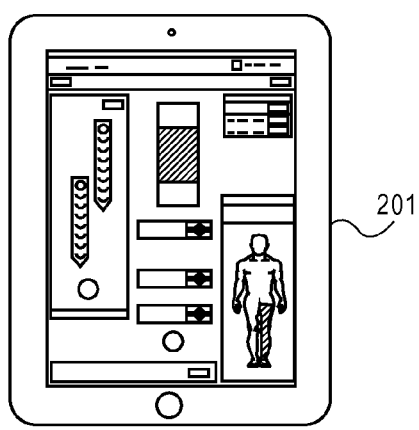

FIG. 1 illustrates a simplified block diagram of a system 100 for initiating a bi-directional communication link. The system 100 may include an implantable medical device (IMD) 101, a triggering device 102 (e.g., a magnet, an inductive communication circuit, a near field communication circuit, an electric motor), and an external device 201 (e.g., table computer, smart phone, laptop, or the like) according to an embodiment. The IMD 101 may be implanted within a patient (e.g., proximate to a heart 103, proximate to the spinal cord). Additionally or alternatively, the IMD 101 may have components that are external to the patient, for example, the IMD 101 may include a neuro external pulse generator (EPG).

The triggering device 102 produces or generates an activation field 109. The IMD 101 may be configured to detect the activation field 109, when the IMD is passed through and/or placed within the activation field 109. The activation field 109 from the triggering device 102 may comprise at least one of a magnetic field, a near field communication transmission, a radio frequency (RF) identification transmission, an inductive telemetry signal, or a vibration scheme resulting in displacement of a position of the IMD 101. The activation field 109 may be defined by the affective distance or area from the triggering device 102 where the activation field 109 may be detected by the IMD 101. Optionally, the triggering device 102 may continually produce or emit the activation field 109. For example, the activation field 109 may include a magnetic field generated by a magnet of the triggering device 102. Additionally or alternatively, the activation field 109 may be activated by a user. For example, the activation field 109 may include a near field communication (NFC) transmission generated by an NFC circuit of the triggering device 102, which is activated by the user when positioned proximate to the IMD 101.

When the activation field 109 is detected by the IMD 101, the IMD 101 may be programmed and/or configured to enter a select communication initialization mode corresponding to the activation field 109 detected from the triggering device 102. The select communication initialization mode may be a subset of a plurality of communication initialization modes defined by the wireless protocol to establish a bi-directional communication link 104 between the IMD 101 and the external device 201. For example, the communication initialization mode may correspond to a defined pairing and/or bonding procedure. Optionally, the communication initialization mode may by the IMD 101 from a sleeping and/or power saving state by activating a radio frequency (RF) circuit 110.

Additionally or alternatively, the IMD 101 may determine which communication initialization mode is selected based on a field characterization of the activation field, such as, a strength, frequency, phase and/or select characteristic value of the activation field 109. For example, the IMD 101 may identify a magnetic field strength and/or flux of the activation field 109 at a first value corresponding to a communication initialization mode for initiating the pairing and/or bonding procedure between the IMD 101 and the external device 201.

In another example, the IMD 101 may detect a magnetic field strength and/or flux of the activation field 109 at a second value corresponding to a communication initialization mode for activating the RF circuit 110 of the IMD 101 for reestablishing the bi-directional communication link 104 with a previously bonded and/or paired external device 201.

The external device 201 is configured to establish the bi-directional communication link 104 with the IMD 101. The communication link 104 allows the external device 201 to receive measurements from the IMD 101, and to program or send instructions to the IMD 101. The bi-directional communication link 104 may use any standard wireless protocol such as Bluetooth Low Energy, Bluetooth, Wireless USB, Medical Implant Communication Service, ZigBee, and the like. The external device 201 may be located within a home of the patient, a hospital, an automobile, at an office of the patient, or the like. The IMD 101 may be one of various types of implantable devices, such as, for example, neurostimulator, electrophysiology (EP) mapping and radio frequency (RF) ablation system, an implantable pacemaker, implantable cardioverter-defibrillator (ICD), defibrillator, cardiac rhythm management (CRM) device, an implantable pulse generator (IPG), or the like (FIG. 2).

Figure 2:
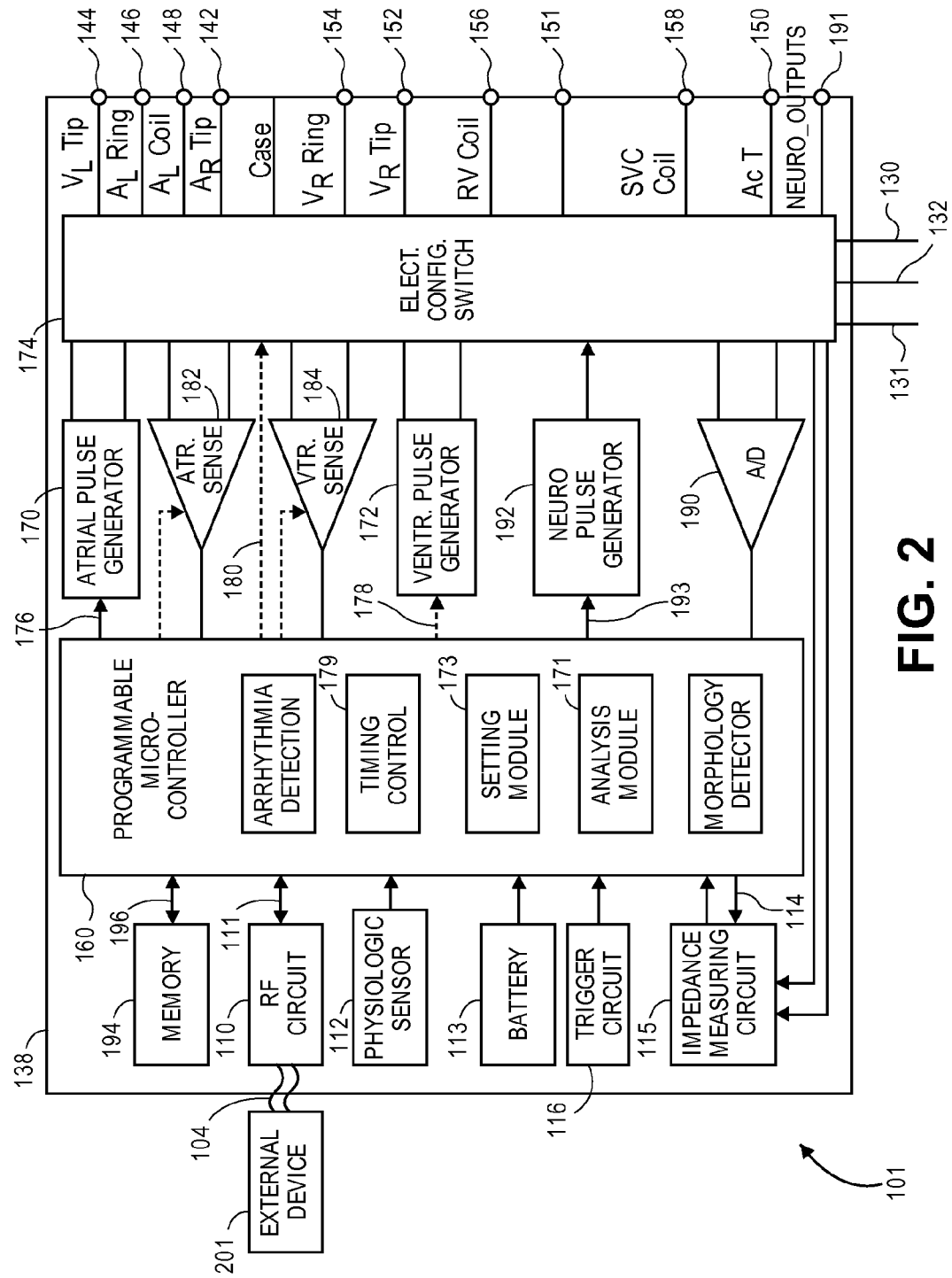
FIG. 2 illustrates a block diagram of exemplary internal components of an implantable medical device, according to an embodiment of the present disclosure.

FIG. 2 illustrates a block diagram of exemplary internal components of the IMD 101. The systems described herein can include or represent hardware and associated instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. These devices may be off-the-shelf devices that perform the operations described herein from the instructions described above. Additionally or alternatively, one or more of these devices may be hard-wired with logic circuits to perform these operations.

The IMD 101 is for illustration purposes only, and it is understood that the circuitry could be duplicated, eliminated or disabled in any desired combination to provide a device capable of treating the appropriate chamber(s) with cardioversion, defibrillation and/or pacing stimulation as well as providing for apnea detection and therapy. Additionally or alternatively, the IMD 101 may be used to generate electrical stimulation for application to a desired area of a body, such as a spinal cord stimulation, as described later herein corresponding to FIG. 8.

The housing 138 for the IMD 101, shown schematically in FIG. 2, is often referred to as the "can", "case" or "case electrode" and may be programmably selected to act as the return electrode for all "unipolar" modes. The housing 138 may further be used as a return electrode alone or in combination with one or more of the coil electrodes for shocking purposes. The housing 138 further includes a connector (not shown) having a plurality of terminals, 142, 152, 154, 156 and 158 (shown schematically and, for convenience, the names of the electrodes to which they are connected are shown next to the terminals. A right atrial tip terminal ($A_R$ TIP) 142 is adapted for connection to the atrial tip electrode and a right atrial ring terminal may be adapted for connection to right atrial ring electrode. A left ventricular tip terminal ($V_L$ TIP) 144, a left atrial ring terminal ($A_L$ RING) 146, and a left atrial shocking terminal ($A_L$ COIL) 148 are adapted for connection to the left ventricular ring electrode, and a left atrial tip electrode and a left atrial coil electrode respectively. A right ventricular tip terminal ($V_R$ TIP) 152, a right ventricular ring terminal ($V_R$ RING) 154, a right ventricular shocking terminal (R$_V$ COIL) 156, and an SVC shocking terminal (SVC COIL) 158 are adapted for connection to the right ventricular tip electrode, right ventricular ring electrode, an RV coil electrode, and an SVC coil electrode, respectively.

An acoustic terminal (ACT) 150 is adapted to be connected to an external acoustic sensor or an internal acoustic sensor, depending upon which (if any) acoustic sensors are used. Terminal 151 is adapted to be connected to a blood sensor to collect measurements associated with glucose levels, natriuretic peptide levels, or catecholamine levels.

The IMD 101 includes a programmable microcontroller 160 which controls operation. The microcontroller 160 (also referred to herein as a processor module or unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 160 includes the ability to process or monitor input signals (data) as controlled by program code stored in memory. The details of the design and operation of the microcontroller 160 are not critical to the invention. Rather, any suitable microcontroller 160 may be used that carries out the functions described herein. Among other things, the microcontroller 160 receives, processes, and manages storage of digitized cardiac data sets from the various sensors and electrodes. For example, the cardiac data sets may include IEGM data, pressure data, heart sound data, and the like.

The IMD 101 includes an atrial pulse generator 170 and a ventricular/impedance pulse generator 172 to generate pacing stimulation pulses for delivery by the right atrial lead 130, the right ventricular lead 131, and/or the coronary sinus lead 132 via an electrode configuration switch 174. It is understood that in order to provide stimulation therapy in each of the four chambers of the heart, the atrial and ventricular pulse generators, 170 and 172, may include dedicated, independent pulse generators, multiplexed pulse generators or shared pulse generators. The pulse generators, 170 and 172, are controlled by the microcontroller 160 via appropriate control signals, 176 and 178, respectively, to trigger or inhibit the stimulation pulses.

The IMD 101 includes a neuro stimulation pulse generator circuit 192 to generate stimulation pulses for a brain or spinal cord nervous system. The stimulation pulses are delivered by a plurality of electrodes through the neuro output lead 191. The neuro stimulation pulse generator circuit 192 is controlled by the microcontroller 160 via appropriate control signals 193 to trigger or generate the stimulation pulses.

The microcontroller 160 further includes timing control circuitry 179 used to control the timing of such stimulation pulses (e.g., pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. Switch 174 includes a plurality of switches for connecting the desired electrodes to the appropriate I/O circuits, thereby providing complete electrode programmability. Accordingly, the switch 174, in response to a control signal 180 from the microcontroller 160, determines the polarity of the stimulation pulses (e.g., unipolar, bipolar, etc.) by selectively closing the appropriate combination of switches (not shown) as is known in the art.

Atrial sensing circuit 182 and ventricular sensing circuit 184 may also be selectively coupled to the right atrial lead 130, coronary sinus lead 132, and the right ventricular lead 131, through the switch 174 for detecting the presence of cardiac activity in each of the four chambers of the heart. Accordingly, the atrial (ATR SENSE) and ventricular (VTR SENSE) sensing circuits, 182 and 184, may include dedicated sense amplifiers, multiplexed amplifiers or shared amplifiers. The outputs of the atrial and ventricular sensing circuits, 182 and 184, are connected to the microcontroller 160 which, in turn, are able to trigger or inhibit the atrial and ventricular pulse generators, 170 and 172, respectively, in a demand fashion in response to the absence or presence of cardiac activity in the appropriate chambers of the heart.

Cardiac signals are also applied to the inputs of an analog-to-digital (A/D) data acquisition system 190. The data acquisition system 190 is configured to acquire IEGM signals, convert the raw analog data into a digital IEGM signal, and store the digital IEGM signals in memory 194 for later processing and/or RF transmission to the external device 201. The data acquisition system 190 is coupled to the right atrial lead 130, the coronary sinus lead 132, and the right ventricular lead 131 through the switch 174 to sample cardiac signals across any combination of desired electrodes. The data acquisition system 190 may also be coupled, through switch 174, to one or more of the acoustic sensors. The data acquisition system 190 acquires, performs A/D conversion, produces and saves the digital pressure data, and/or acoustic data.

The controller 160 controls the acoustic sensor and/or a physiologic sensor to collect heart sounds during one or more cardiac cycles. The heart sounds include sounds representative of a degree of blood flow turbulence. The acoustic sensor and/or physiologic sensor collects the heart sounds that include S1, S2 and linking segments. The S1 segment is associated with initial systole activity. The S2 segment is associated with initial diastole activity. The linking segment is associated with at least a portion of heart activity occurring between the S1 and S2 segments during a systolic interval between the initial systole and diastole activity. The controller 160 changes a value for at least one of the pacing parameters between the cardiac cycles. The controller 160 implements one or more processes described herein to determine values for one or more pacing parameters that yield a desired level of hemodynamic performance.

The controller 160 includes an analysis module 171 and a setting module 173 that function in accordance with embodiments described herein. The analysis module 171 analyzes a characteristic of interest from the heart sounds within at least a portion of the linking segment. The characteristic of interest is indicative of an "amount" of the heart sounds over at least a portion of the systolic interval between the initial systole and diastole activity. The amount of the heart sounds may be derived in different manners, such as determining the energy content, intensity and the like, as well as relations there between. The level of the characteristic changes as the pacing parameter is changed. The setting module 173 sets a desired value for the pacing parameter based on the characteristic of interest from the heart sounds for at least the portion of the linking segment. The pacing parameter may represent at least one of an AV delay, a VV delay, a VA delay, intra-ventricular delays, electrode configurations and the like. The controller 160 changes at least one of the AV delay, the VV delay, the VA delay, the intra-ventricular delays, electrode configurations and like in order to reduce systolic turbulence and regurgitation.

The RF circuit 110 may be configured to handle and/or manage the bi-directional communication link between the IMD 101 and the external device 201. The RF circuit 110 is controlled by the microcontroller 160 and may support a particular wireless communication protocol while communicating with the external device 201, such as Bluetooth low energy, Bluetooth, ZigBee, Medical Implant Communication Service (MICS), or the like. Protocol firmware may be stored in memory 194, which is accessed by the microcontroller 160. The protocol firmware provides the wireless protocol syntax for the controller 160 to assemble data packets, establish communication links 104, and/or partition data received from the external device 201.

The microcontroller 160 may be coupled to a trigger circuit 116 that functions in accordance with embodiments described herein. The trigger circuit 116 may include a Hall Effect sensor, MEMS sensor, an inductor, an inductive telemetry antenna, an accelerometer, an NFC receiver, and/or the like. Optionally, the trigger circuit 116 may include amplifiers, analog to digital converters, memory storage devices, digital signal processors, or the like. Additionally or alternatively, all or portions of the trigger circuit 116 may be integrated within the RF circuit 110 and/or the microcontroller 160. The trigger circuit 116 may be monitored by the microcontroller 160 to detect the presence of the activation field 109 generated by the triggering device 102 and/or to identify field characterization of the activation field 109. Optionally, the trigger circuit 116 may change an electrical potential (e.g., voltage) signal to the microcontroller 160 when a portion of the activation field 109 overlaps the IMD 101.

For example, the trigger circuit 116 measures an induced magnetic field upon the IMD 101. The trigger circuit 116 may measure and/or store measurements, such as field characterization measurements of the induced magnetic field, to memory 194 or output to the microcontroller 160. The trigger circuit 116 and/or microcontroller 160 may compare one or more of the field characterization measurements (e.g., magnetic field strength, flux) of the induced magnetic field with previously stored measured magnetic fields and/or a predetermined threshold to verify that the induced magnetic field corresponds to the activation field 109 generated by the triggering device 102 and is not noise or magnetic interference. For example, if the trigger circuit 116 determines that the field characterization measurements are above the predetermined threshold the field characterization measurements are verified by the trigger circuit 116 as corresponding to the activation field 109. When the trigger circuit 116 confirms and/or verifies that the induced magnetic field corresponds to the activation field 109, the trigger circuit 116 may output a detection signal to the microcontroller 160.

In another example, the trigger circuit 116 may measure an inductive telemetry signal corresponding to the activation field 109 from an inductive telemetry antenna of the trigger circuit 116. The telemetry signal changes the inductive coupling between the triggering device 102 and the inductive telemetry antenna of the trigger circuit 116. The trigger circuit 116 measures an electrical change caused by the inductive coupling, such as a voltage or a current change from the output of the inductive telemetry antenna, to determine the telemetry signal. Optionally, the trigger circuit 116 may output the electrical change measurements to the microcontroller 160. The trigger circuit 116 and/or microcontroller 160 may compare the measured telemetry signal with a predetermined telemetry signal stored in memory 194 to verify that the inductive telemetry signal corresponds to the activation field 109, the trigger circuit 116 may output a detection signal to the microcontroller 160.

In another example, the trigger circuit 116 may measure an RFID signal corresponding to the activation field 109. Optionally, the RFID signal may include a unique identifier, such as a string of characters (e.g., numerals, letters, control codes, spaces) corresponding to a communication initialization mode of the wireless protocol for the IMD 101 stored on the memory 194. Additionally or alternatively, the RFID signal may be based on an NFC protocol such as a short range wireless communication protocol or NFC transmission defined in ISO/IEC 18092/ECMA-340, ISO/IEC 21481/ECMA-352, ISO/IEC 14443, or the like. Optionally, once the RFID signal is received by the trigger circuit 116, the trigger circuit 116 may output the RFID signal to the microcontroller 160. The trigger circuit 116 and/or the microcontroller 160 may compare the unique identifier of the RFID signal with stored identification signals on memory 194 to select a communication initialization mode. The stored identification signals may be included within a table or list with corresponding communication initialization modes of the wireless protocol.

In another example, the trigger circuit 116 may measure shifts and/or changes in position of the IMD 101 from a vibration scheme corresponding to the activation field 109. Optionally, the vibration scheme may correspond to a communication initialization mode of the wireless protocol for the IMD 101 stored on the memory 194. The shifts and/or changes in position of the IMD 101 may be measured by an accelerometer of the trigger circuit 116. Optionally, the trigger circuit 116 may output position measurements of the IMD 101 to the microcontroller 160. The trigger circuit 116 and/or microcontroller 160 may compare the changes in the position measurements of the IMD 101 to determine a speed and/or pattern corresponding to the vibration scheme resulting from the activation field 109. The trigger circuit 116 and/or the microcontroller 160 may compare the measured vibration scheme to a stored vibration scheme on the memory 194 to select a communication initialization mode.

The microcontroller 160 is coupled to memory 194 by a suitable data/address bus 196, wherein the programmable operating parameters used by the microcontroller 160 are stored and modified, as required, in order to customize the operation of IMD 101 to suit the needs of a particular patient. The memory 194 also stores data sets (raw data, summary data, histograms, etc.), such as the IEGM data, heart sound data, pressure data, Sv02 data and the like for a desired period of time (e.g., 1 hour, 24 hours, 1 month). The memory 194 may store instructions to direct the microcontroller 160 to analyze the cardiac signals and heart sounds identify characteristics of interest and derive values for predetermined statistical parameters. The IEGM, pressure, and heart sound data stored in memory 194 may be selectively stored at certain time intervals, such as 5 minutes to 1 hour periodically or surrounding a particular type of arrhythmia of other irregularity in the heart cycle. For example, the memory 194 may store data for multiple non-consecutive 10 minute intervals.

The memory 194 may also contain a pre-defined algorithm that generates a passkey. The passkey may be used during a pairing and/or bonding procedure between the IMD 101 and the external device 201 to establish a bi-directional communication link over the communication link 104. The passkey may be generated based on passkey seed information. The passkey seed information may include a dynamic seed and/or a static identification or encrypted static identification transmitted by the RF circuit 110 through the communication link 104 from the external device 201 and inputted into the pre-defined algorithm. Optionally, the dynamic seed may be a random number generated by the microcontroller 160, based on the local system clock of the IMD 101, or the like that is transmitted by the RF circuit 110 to the external device 201. Additionally or alternatively, the static identification may be stored on the memory 194 representing a product serial identification number of the IMD 101, which is a unique number assigned to the IMD 101 by a manufacturer of the IMD 101.

Optionally, the static identification may be a pre-determined number stored on the memory 194 set by a clinician.

The pacing and other operating parameters of the IMD 101 may be non-invasively programmed into the memory 194 through the RF circuit 110 in bi-directional wireless communication with the external device 201. The RF circuit 110 is controlled by the microcontroller 160 and receives data for transmission by a control signal 111. The RF circuit 110 allows intra-cardiac electrograms, pressure data, acoustic data, Sv02 data, and status information relating to the operation of IMD 101 (as contained in the microcontroller 160 or memory 194) to be sent to the external device 201 through an established bi-directional communication link 104. The RF circuit 110 also allows the external device 201 to program new pacing parameters for the setting module 173 used by the IMD 101.

To establish the communication link 104 between the external device 201 and the IMD 101, the microcontroller 160 may instruct the RF circuit 110 to transmit an advertisement notice on an advertisement channel corresponding to the select communication initialization mode of the wireless protocol. The advertisement channel is a point to multipoint, unidirectional, channel to carry a repeating pattern of system information messages such as network identification, allowable RF channels to establish the communication link 104, and/or the like that is included within the advertisement notice. The advertisement notice may be repeatedly transmitted after a set duration or an advertisement period until the communication link 104 is established with the external device 201.

The length of the advertisement period may be adjusted by the microcontroller 160 when entering an advertisement mode. During the advertisement mode, the microcontroller 160 may reduce the length of the advertisement period relative to not being in the advertisement mode. The reduced length of the advertisement period results in the RF circuit 110 transmitting more or an increased number of advertisement notices relative to not being in the advertisement mode. The microcontroller 160 may enter the advertisement mode after detecting the activation field 109 corresponding to the select communication initialization mode.

The IMD 101 may also include a physiologic sensor 112, such as an accelerometer commonly referred to as a "rate-responsive" sensor because it is typically used to record the activity level of the patient or adjust pacing stimulation rate according to the exercise state of the patient. Optionally, the physiological sensor 112 may further be used to detect changes in cardiac output, changes in the physiological condition of the heart, or changes in activity (e.g., detecting sleep and wake states) and movement positions of the patient. While shown as being included within IMD 101, it is to be understood that the physiologic sensor 112 may also be external to the IMD 101, yet still be implanted within or carried by the patient. A common type of rate responsive sensor is an activity sensor incorporating an accelerometer or a piezoelectric crystal, which is mounted within the housing 138 of the IMD 101.

The physiologic sensor 112 may be used as the acoustic sensor that is configured to detect the heart sounds. For example, the physiologic sensor 112 may be an accelerometer that is operated to detect acoustic waves produced by blood turbulence and vibration of the cardiac structures within the heart (e.g., valve movement, contraction and relaxation of chamber walls and the like). When the physiologic sensor 112 operates as the acoustic sensor, it may supplement or replace entirely acoustic sensors. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient and, in particular, is capable of detecting arousal from sleep or other movement.

The IMD 101 additionally includes a battery 113, which provides operating power to all of the circuits shown. The IMD 101 is shown as having impedance measuring circuit 115 which is enabled by the microcontroller 160 via a control signal 114. Herein, impedance is primarily detected for use in evaluating ventricular end diastolic volume (EDV) but is also used to track respiration cycles. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 115 is advantageously coupled to the switch 174 so that impedance at any desired electrode may be obtained.

Figure 3:
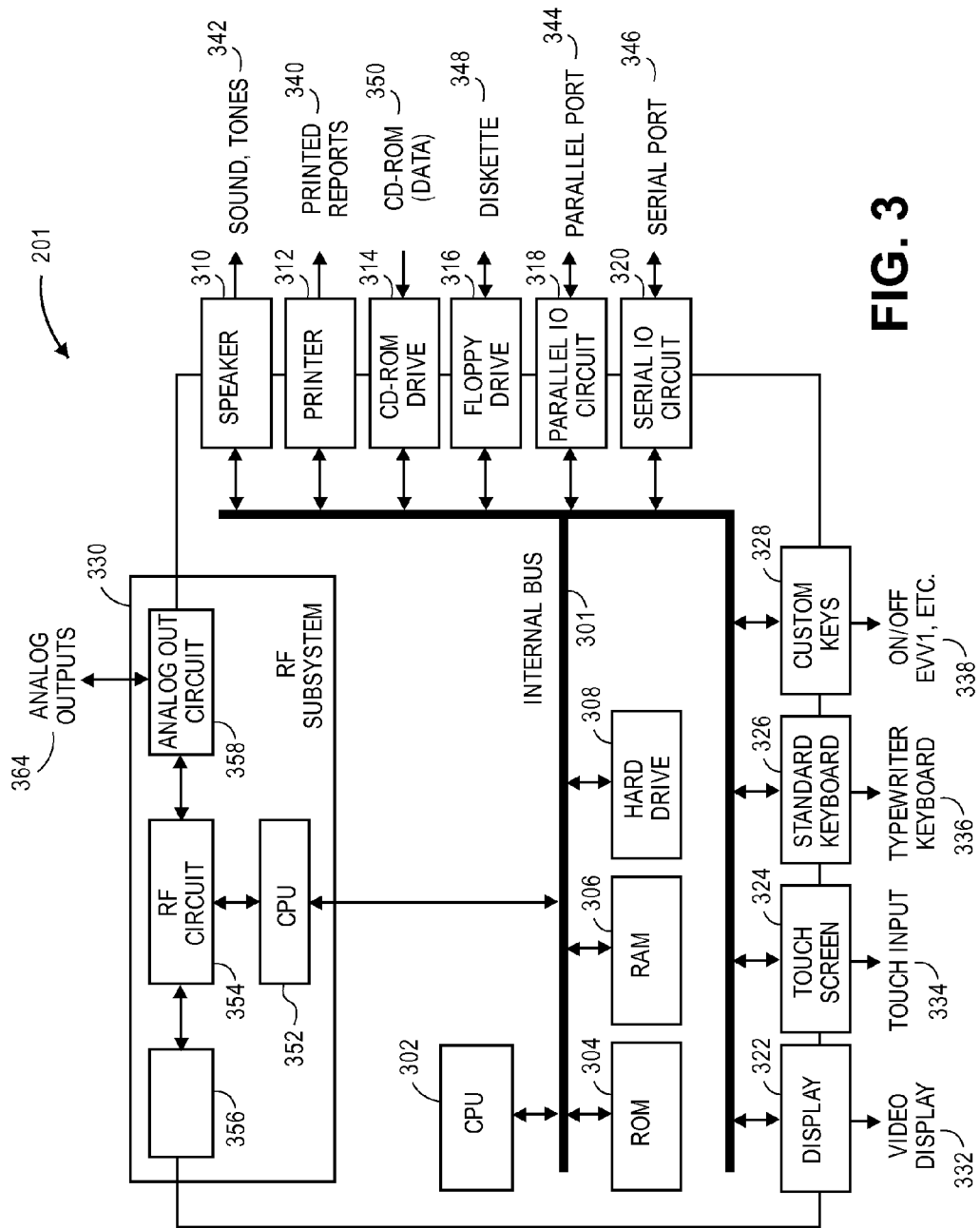
FIG. 3 illustrates a block diagram of exemplary internal components of an external device, according to an embodiment of the present disclosure.

FIG. 3 illustrates a functional block diagram of the external device 201 that is operated in accordance with the processes described herein and to interface with the IMD 101 as described herein. The external device 201 may be a workstation, a portable computer, a tablet computer, an IMD programmer, a PDA, a cell phone and the like. The external device 201 may include an internal bus 301 that may connect/interface with a Central Processing Unit ("CPU") 302, ROM 304, RAM 306, a hard drive 308, a speaker 310, a printer 312, a CD-ROM drive 314, a floppy drive 316, a parallel I/O circuit 318, a serial I/O circuit 320, the display 322, a touchscreen 324, a standard keyboard 326, custom keys 328, and an RF subsystem 330. The internal bus 301 is an address/data bus that transfers information between the various components described herein. The hard drive 308 may store operational programs as well as data, such as stimulation waveform templates and detection thresholds.

The CPU 302 typically includes a microprocessor, a microcontroller, or equivalent control circuitry, designed specifically to control interfacing with the external device 201 and with the IMD 101. The CPU 302 may include RAM or ROM memory, logic and timing circuitry, state machine circuitry, and I/O circuitry to interface with the IMD 101. The display 322 (e.g., may be connected to the video display 332). The display 322 displays various information related to the processes described herein. The touchscreen 324 may display graphic information relating to the IMD 101 and include a graphical user interface. The graphical user interface may include graphical icons, scroll bars, buttons, and the like which may receive or detect user or touch inputs 334 for the external device 201 when selections are made by the user. Optionally the touchscreen 324 may be integrated with the display 322. The keyboard 326 (e.g., a typewriter keyboard 336) allows the user to enter data to the displayed fields, as well as interface with the RF subsystem 330. Furthermore, custom keys 328 turn on/off 338 (e.g., EVVI) the external device 201. The printer 312 prints copies of reports 340 for a physician to review or to be placed in a patient file, and the speaker 310 provides an audible warning (e.g., sounds and tones 342) to the user. The parallel I/O circuit 318 interfaces with a parallel port 344. The serial I/O circuit 320 interfaces with a serial port 346. The floppy drive 316 accepts diskettes 348. Optionally, the serial I/O port may be coupled to a USB port or other interface capable of communicating with a USB device such as a memory stick. The CD-ROM drive 314 accepts CD ROMs 350.

The RF subsystem 330 includes a central processing unit (CPU) 352 in electrical communication with an RF circuit 354, which may communicate with both memory 356 and an analog out circuit 358. The analog out circuit 358 includes communication circuits to communicate with analog outputs 364. The external device 201 may wirelessly communicate with the IMD 101 and utilize protocols, such as Bluetooth, Bluetooth low energy, ZigBee, MICS, and the like. Alternatively, a hard-wired connection may be used to connect the external device 201 to the IMD 101.

Figure 4:
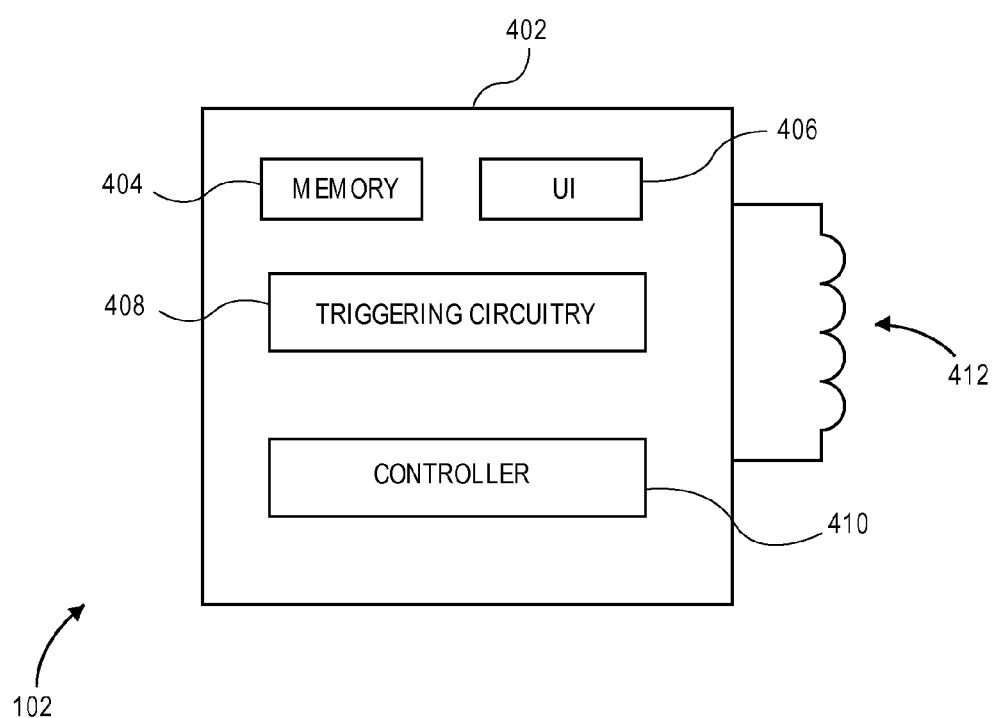
FIG. 4 illustrates a block diagram of exemplary internal components of a triggering device, according an embodiment of the present disclosure.

FIG. 4 illustrates a functional block diagram of the triggering device 102. It should be noted that the triggering device 102 is for illustration purposes only, and it is understood that the circuitry and/or components may be duplicated, eliminated or disabled in any desired combination to generate the activation field 109. For example, in at least one embodiment the triggering device 102 may comprise a magnet (e.g., magnetized metal).

In the illustrated embodiment shown in FIG. 4, the triggering device 102 may include a memory device 404, a controller 410, a user interface device 406, and/or a triggering circuitry 408. The components (e.g., the memory device 404, the triggering circuitry 408, the antenna 412) may be enclosed within a housing 402. The memory device 404 may include flash memory, RAM, ROM, EEPROM, or the like. The user interface device 406 may include a switch, relay, a tactile button, a capacitive button, or the like. The triggering circuitry 408 may be used for generating the activation field 109. For example, the triggering circuitry 408 may include a solenoid or an electromagnetic configuration to generate a magnetic field corresponding to the activation field 109. In another example, the triggering circuitry 408 may include inductive coil circuitry coupled to an antenna 412, such as a telemetry wand. The inductive coil circuitry transmits a telemetry signal through the antenna 412 corresponding to the activation field 109, which changes the inductive coupling between the antenna 412 and the trigger circuit 116.

In another example, the triggering circuitry 408 may include a transmitter or a transmitter and a receiver (e.g., a transceiver) configured to transmit information using an NFC protocol, such as an NFC communication circuit. Optionally, the triggering circuitry 408 may include hardware, such as a processor, controller, or other logic-based device to conform and/or encode information stored in the memory device 404 to the NFC protocol to transmit using the antenna 412, and/or decode information received by the antenna 412 to be processed by the triggering circuitry 408 and/or the controller 410.

In another example, the triggering circuitry 408 may include an electric motor such as a vibration motor that includes a DC motor with an offset mass or weight attached to the shaft. A speed and/or direction of the shaft of the vibration motor may be controlled by a signal output from the controller 410. The offset mass on the shaft causes the motor to be displaced or vibrate. Optionally, the signal output of the controller 410 may be activated by a clinician or user through the user interface device 406. Additionally or alternatively, the signal output may correspond to a vibration scheme stored on the memory device 404 resulting in vibrations of the triggering device 102 which may displace and/or change a position of the IMD 101.

Figure 5:
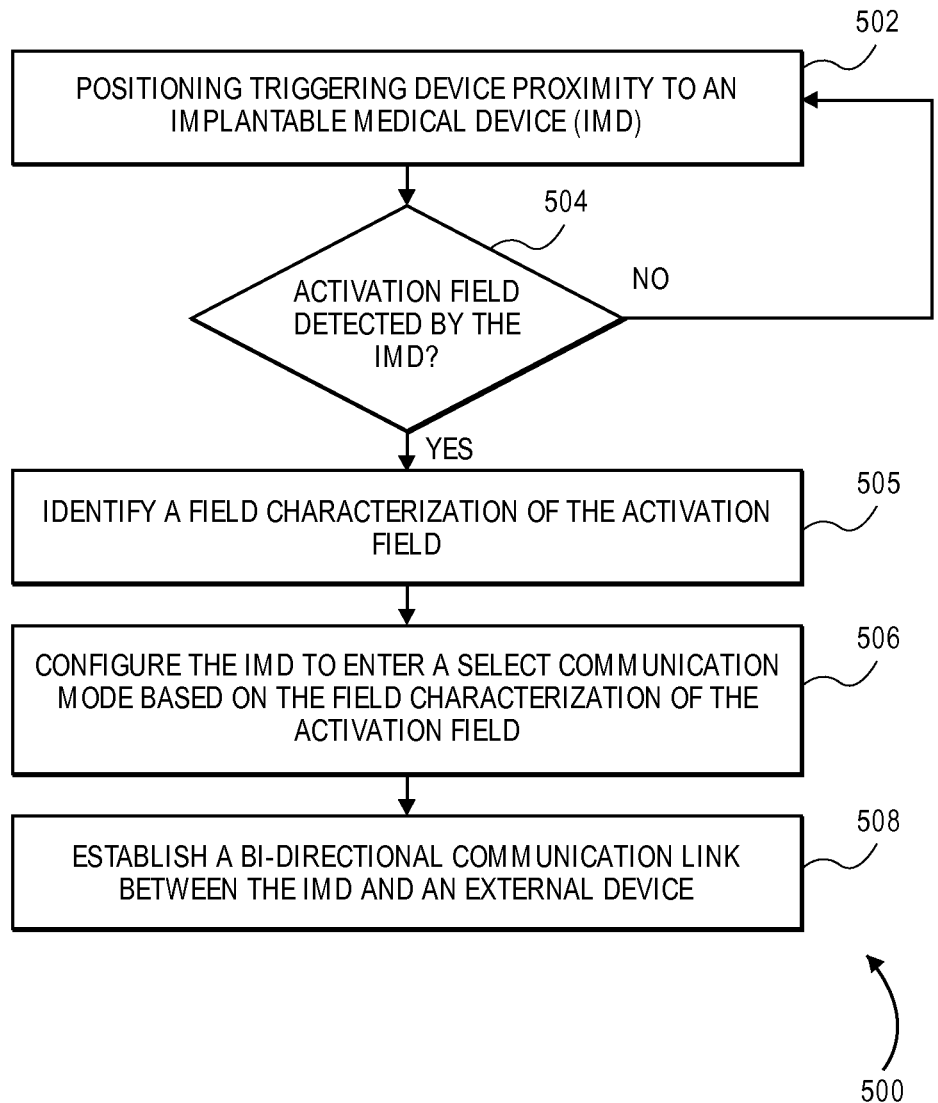
FIG. 5 illustrates a flowchart of a method for initiating a bi-directional communication link with an implantable medical device.

FIG. 5 illustrates a flowchart of a method 500 for initiating a bi-directional communication link with an IMD (e.g., 101). The method 500 may be implemented as a software algorithm, package, or system that directs one or more hardware circuits or circuitry to perform the actions described herein. For example, the operations of the method 500 may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

At least one technical effect of at least one portion of the methods described herein includes establishing a communication link by i) configuring an implantable medical device (IMD) to detect an activation field from a triggering device when the triggering device 102 is positioned proximate to the IMD, ii) configuring the IMD to identify a field characterization of the activation field, and iii) configuring the IMD to establish a bi-directional communication link with an external device through a select communication initialization mode from a plurality of communication initialization modes defined by a wireless protocol in response to the field characterization of the activation field.

Beginning at 502, the triggering device 102 may be positioned proximate to the IMD 101. For example, the triggering device 102 may be positioned such that the IMD 101 is within and/or is overlapped with the activation field 109.

At 504, the IMD 101 may determine whether the activation field 109 is detected. For example, the trigger circuit 116 of the IMD 101 may be configured to detect the activation field 109 from the triggering device 102 when positioned proximate to the IMD 101.

When the activation field is detected by the trigger circuit 116, at 505, the field characterization of the activation field may be identified. In at least one embodiment, the IMD 101 may identify a field characterization of the activation field 109. For example, the field characterization may be identified and/or measured by the trigger circuit 116. The activation field 109 may be configured by the triggering circuitry 408 have a field characterization that corresponds to a select or one communication initialization mode from a plurality of communication initialization modes defined by the wireless protocol. The field characterization may represent a strength, phase, frequency, or the like of the activation field 109. For example, the triggering circuitry 408 may adjust a strength of the magnetic field based on which of the available communication initialization modes of the wireless protocol is used for establishing the bi-directional communication link between the IMD 101 and the external device 201. Optionally, the triggering circuitry 408 may include unique identifiers within an RFID signal or an inductive telemetry signal that corresponds to the select communication initialization mode. In another example, the triggering circuitry 408 may drive the triggering device 102 to generate a vibration scheme of the activation field 109 corresponding to the select communication initialization mode.

At 506, the IMD 101 may be configured to enter a select communication initialization mode based on the field characterization of the activation field 109. The select communication initialization mode may correspond to a defined pairing procedure of the wireless protocol. In another example, the select communication initialization mode may correspond to the IMD 101 re-establishing a communication link with a previously paired and/or bonded external device 201.

In at least one embodiment, the triggering device 102 can generate a static activation field that corresponds to the select communication initialization mode. For example, the triggering device 102 may comprise a magnet (e.g., magnetized metal) that produces a static magnetic field. The magnetic field may be used as the activation field 109, which has a predetermined strength and/or magnetic flux that corresponds to the select communication initialization mode. For example, the magnetic field generated by the magnet may correspond to the select communication initialization mode of the defined pairing procedure of the wireless protocol. Thereby the IMD 101 initiates the defined pairing procedure when the magnetic field is identified.

Optionally, the IMD 101 may exit a communication sleep mode when the activation field 109 is detected. During the communication sleep mode the RF circuit 110 may be disabled or idle such that the RF circuit 110 is not transmitting and/or receiving communications. The IMD 101 may be configured and/or programmed to activate the RF circuit 110 when the corresponding activation field 109 is detected. A technical effect of the communication sleep mode allows the IMD 101 to conserve power and/or increase power efficiency by deactivating components (e.g., the RF circuit 110) when not in use.

At 508, when the IMD 101 enters the select communication initialization mode the IMD 101 may establish a bi-directional communication link between the IMD and the external device 201 through a wireless protocol (e.g., Bluetooth low energy, Bluetooth). In at least one embodiment, the IMD 101 may be configured to establish a bi-directional communication link with the external device 201 through a select communication initialization mode from a plurality of communication initialization mode defined by the wireless protocol in response to the field characterization of the activation field 109. The RF circuit 110 of the IMD 101 and the RF circuit 354 of the external device 201 may be configured to communicate utilizing Bluetooth Low Energy (or Bluetooth Smart), Bluetooth, MICS, ZigBee, or the like. Examples of forming a communication link between an IMD and an external device is disclosed in U.S. patent application Ser. No. 14/091,809, entitled, "SYSTEM AND METHODS FOR ESTABLISHING A COMMUNICATION SESSION BETWEEN AN IMPLANTABLE MEDICAL DEVICE AND AN EXTERNAL DEVICE," which is expressly incorporated herein by reference.

Figure 6:
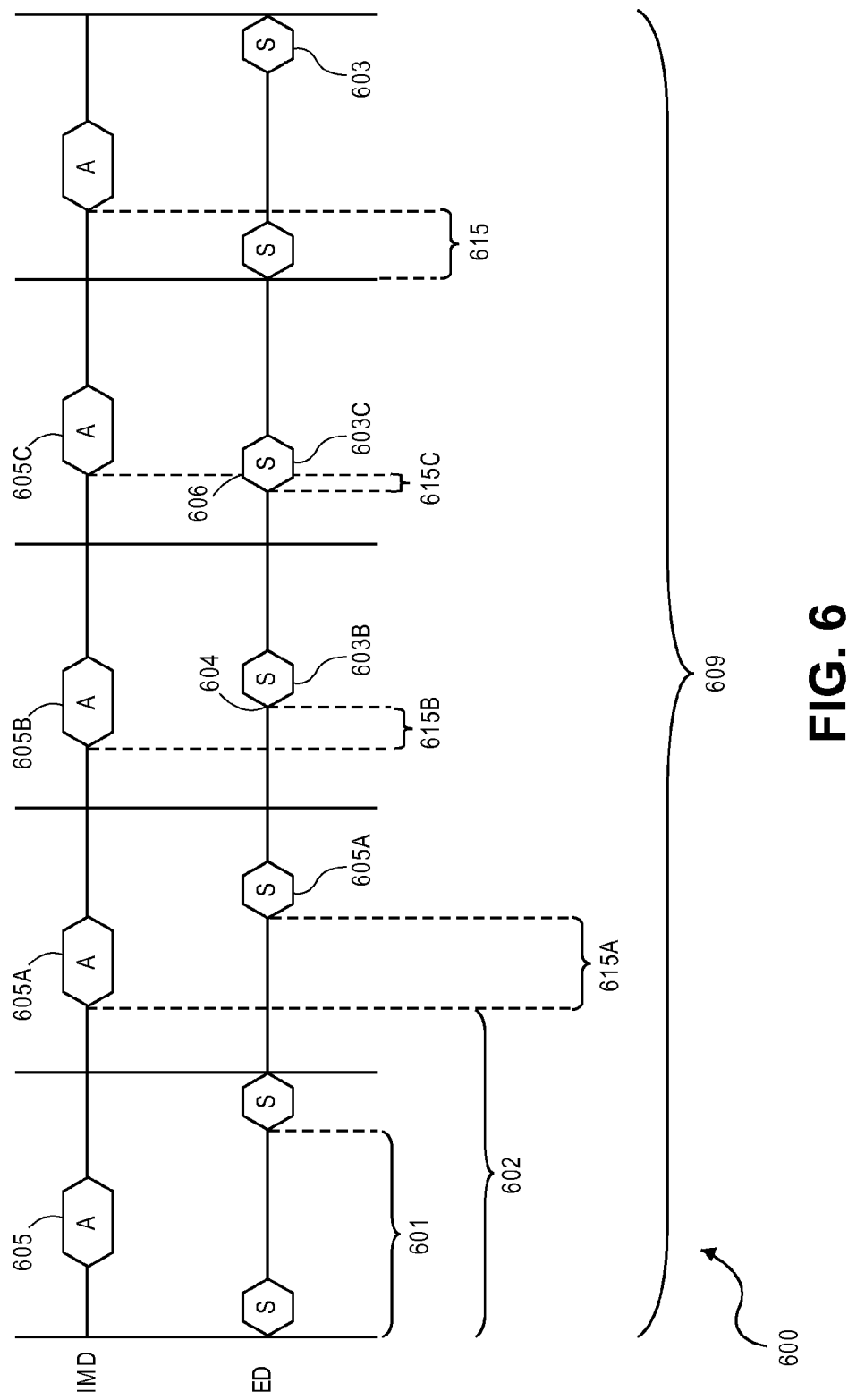
FIG. 6 illustrates a timing diagram between an implantable medical device and an external device to establish a communication link, according to an embodiment of the present disclosure.

For example, FIG. 6 illustrates a timing diagram 600 between the IMD 101 and the external device 201 to establish the communication link 104, according to an embodiment of the present disclosure. The IMD 101 and the external device 201 use a wireless protocol (e.g., Bluetooth low energy) that utilizes a specified frequency for an advertisement channel. The IMD 101 transmits an advertisement notice 605 on the advertisement channel using the RF circuit 110 corresponding to the select communication initialization mode. For example, when the select communication initialization mode corresponds to the defined pairing and/or bonding procedure, the advertisement notice 605 may include pairing and/or bondable information (e.g., passkey seed information). Additionally or alternatively, the advertisement notice may contain frequency synchronization information utilized to form the communication link 104, address information of the IMD 101, address information of the external device 201, and the like. The advertisement notice 605 may be repeated, at a set or variable interval or advertisement period 602, until the communication link 104 is established. The advertisement period 602 represents the length of time the IMD 101 may transmit another advertisement notice 605 after a previous transmission by the IMD 101 of the advertisement notice 605. Optionally, the advertisement period 602 may be input by a user (e.g., physician using an external device).

The advertisement period 602, for example, may be 5 seconds such that the advertisement notice 605 may be repeated every 5 seconds. Optionally, the advertisement period 602 may be longer or shorter than the above example. Additionally or alternatively, the advertisement period may be predetermined and stored in memory 194 of the IMD 101.

The user, using the touchscreen 324 or standard keyboard 336, may instruct the external device 201 to establish the communication link 104 with the IMD 101. The CPU 302 instructs the RF subsystem 330 to output the received transmissions from the advertisement channel (e.g., 2402 MHz, 2426 MHz, 2480 MHz), for example, every 1 s. The output of the RF subsystem 330 corresponds to a scanning interval 603. The RF subsystem repeats the scanning interval 603 every scan period 601 such that the scanning interval 603 may be repeated, for example, every 4 s. The scanning interval 603 and/or scan period 601 may be longer or shorter than the above example. Additionally or alternatively, the scanning interval 603 and/or scan period 601 may be a predetermined length stored on the ROM 304, the RAM 306, or the hard drive 308. Optionally, the scanning interval 603 and/or scan period 601 is configured by the user, such that, the scanning interval 603 or period 601 may be increased or decreased. The RF subsystem 330 continually repeats the scanning interval 603 until the CPU 302 acknowledges receipt of the advertisement notice 605.

The scan period 601 and the advertisement period 602 occur independent and asynchronous with respect to one another, such that the advertisement notices 605 intermittently overlap the scan intervals at 604 and 606. Each period length is predetermined from distinct and separate sources. The scan period 601 is predetermined or configured by the user of the external device 201. Separately, the advertisement period 602 is predetermined by the protocol syntax stored in the memory 194 of the IMD 101. One of the scan period 601 and the advertisement period 602 may be altered, while, the length of the other period (e.g., advertisement period 602, scan period 601) remains constant.

The scan period 601 has an asynchronous phased relation with respect to the advertisement period 602 in order that a phase interval 615 between beginnings of the scanning intervals 603 and advertisement notices 605 continuously (or intermittently) changes. For example, the scan period 601 may be 4 s having the scanning interval 603 of 1 s, and advertisement period 602 may be 5 s having the advertisement notice 605 of 1.5 s. The different lengths of the periods 601 and 602 represent the asynchronous phased relationship with respect to each other. The asynchronous phased relationship causes the advertisement notice 605 and the scanning interval 603 to begin at different times thus creating phase intervals 615. The length of the phase interval 615 can be extended or shortened by changing the advertisement period 602 of the IMD 101 or the scan period 601 of the external device 201. Thus, by configuring the advertisement period 602 or the scan period 601, the phase interval 615 may continuously change or be changed intermittently after a set number of cycles. The beginning of the cycle occurs at the transmission of the advertisement notice 605 or the scan interval 603. The phase interval 615 may be controlled by the user changing the scan period 603 of the external device 201 or by the microcontroller 160 changing the advertisement period 602 of the IMD 101.

For example, the phase interval 615 of the timing diagram 600, is continuously changing after each cycle. The phase interval 615*a*, measured between the beginning of the advertisement notice 605*a* and the beginning of the scan interval 603*a*, may be approximately 1.5 s. The advertisement notice 605*a* and the scanning interval 603*a* do not partially or wholly overlap. The phase interval 615*b*, between the advertisement notice 605*b* and the scanning interval 603*b*, may be approximately 750 ms. The phase interval 615*c*, between the advertisement notice 605*c* and the scanning interval 603*c*, may be approximately 250 ms. Accordingly, the length of the phase interval 615 continuously changes each cycle. The changes in the length of the phase interval 615 cooperate such that each cycle or repetition of the scanning interval 603 and the advertisement notice 605 shifts with respect to each other, thereby allowing for partially overlapping events at 604 and 606 to occur. For instance, only the phase intervals 615*b*-615*c* are associated with partially overlapping advertisement notices 605*b*-*c* and scanning intervals 615*b*-*c*. Although the periods 601, 602 are asynchronous, the scanning intervals 603 and the advertisement notices 605 will partially overlap and enable the external device 201 intermittently or after a set number of cycles to receive the advertisement notice 605. The overlaps occur intermittently, in that after a number of cycles the scanning interval 603 and advertisement notice 605 will partially overlap in fewer cycles than the number of cycles. For example, the scanning interval 603 and advertisement notice 605 partially overlap after the fourth and fifth cycle of the scanning interval 603 or the third and fourth cycle of the advertisement notice 605.

Optionally, the IMD 101 may have an advertisement mode that decreases the number of cycles needed until the communication link 104 is established, by increasing the likelihood of the scanning interval 603 partially overlapping the advertisement notice 605. During an advertisement mode, the microcontroller 160 may decrease the length of the advertisement period 602, relative to not being in the advertisement mode, thereby, increasing the number of advertisement notices 605 in a time frame 609. The increased number of advertisement notices 605 increase the number of partial overlaps with the scanning intervals 603, allowing the external device 201 to detect or receive the advertisement notice 605 in a shorter amount of cycles relative to the IMD 101 that is not in an advertisement mode.

Optionally, the IMD 101 may be programmed and/or configured to disable the RF circuit 110 and/or end or terminate the select communication initialization mode when a connection request is not received within a predetermined period. The predetermined period may be stored on the memory 194, defined by the wireless protocol, connected to the select communication initialization mode, or the like. For example, the IMD 101 may stop transmitting advertisement notices 605 after the predetermined period, such as five minutes. It should be noted that in other embodiments the predetermined period may be greater than or lesser than five minutes. In another example, the IMD 101 may enter into the communication sleep mode after the predetermined period. During the communication sleep mode the RF circuit 110 may be disabled or idle such that the RF circuit 110 is not transmitting and/or receiving communications.

Once the external device 201 receives the advertisement notice 605, in the form of a data packet transmitted from the IMD 101, the CPU 302 analyzes or compares the data packet with the protocol syntax stored on the ROM 304, the RAM 306, or the hard drive 308. The protocol syntax may include the structure of an advertisement notice (e.g., data packet specifications, appropriate number of bits, frequency, or the like) utilized by the wireless protocol. Optionally, the advertisement notice 605 may include a unique code designating the packet as an advertisement. By comparing the protocol syntax with the data packet, the CPU 302 determines whether the received data packet is an advertisement notice 605 using the wireless protocol of the external device 201. If the received data packet is determined not to be an advertisement notice, the external device 201 may continue scanning the advertisement channel. When the CPU 302 determines that the data packet received by the RF circuit 354 is the advertisement notice 605 (having the proper syntax), the CPU 302 outputs a connection request (e.g., data packet) to be transmitted by the RF circuit 354 along the advertisement channel.

The CPU 302 constructs a data packet representing the connection request by adding packet frames to conform to the protocol such as the address of the IMD 101 and/or external device 201, error detection codes such as CRC, a payload, or the like. The payload may include connection instructions (e.g., frequency of the data channel for the communication link 104) from the user intended for the IMD 101. Optionally, the data packet may include a static identification of the external device 201 and a dynamic seed. Once the data packet has been formed, the CPU 302 outputs the data packet to the RF subsystem 330 to be transmitted along the advertisement channel that was to the IMD 101.

The RF circuit 110 receives the data packet and outputs to the microcontroller 160. The microcontroller 160 may store the data packet in memory 194 for analysis. The microcontroller 160 determines whether the data packet is in response to the advertisement notice 605 by comparing the address information of the data packet with the address transmitted by the IMD 101 within the advertisement notice 605. If the address information matches, the microcontroller 160 partitions the payload from the data packet.

When the select communication initialization mode corresponds to re-establishing a communication link with a previously paired and/or bonded external device 201, the microcontroller 160 may compare the address information of the external device 201 on the data packet with a previously paired and/or bonded links table stored in memory 194. The previously paired and/or bonded links table may be used to determine whether the IMD 101 has previously paired and/or bonded with the external device 201. For example, if the IMD 101 determines that the external device 201 corresponds to an un-paired and/or un-bonded external device (e.g., not previously paired) the IMD 101 may ignore the connection request from the external device 201. In another example, if the IMD 101 determines that the external device 201 was paired or bonded previously may partition the payload of the data packet. Once the microcontroller 160 identifies the connection request, the microcontroller 160 may instruct the RF circuit 110 to monitor the data channel identified in the connection request for further instructions from the external device 201, establishing the communication link 104.

Figure 7:
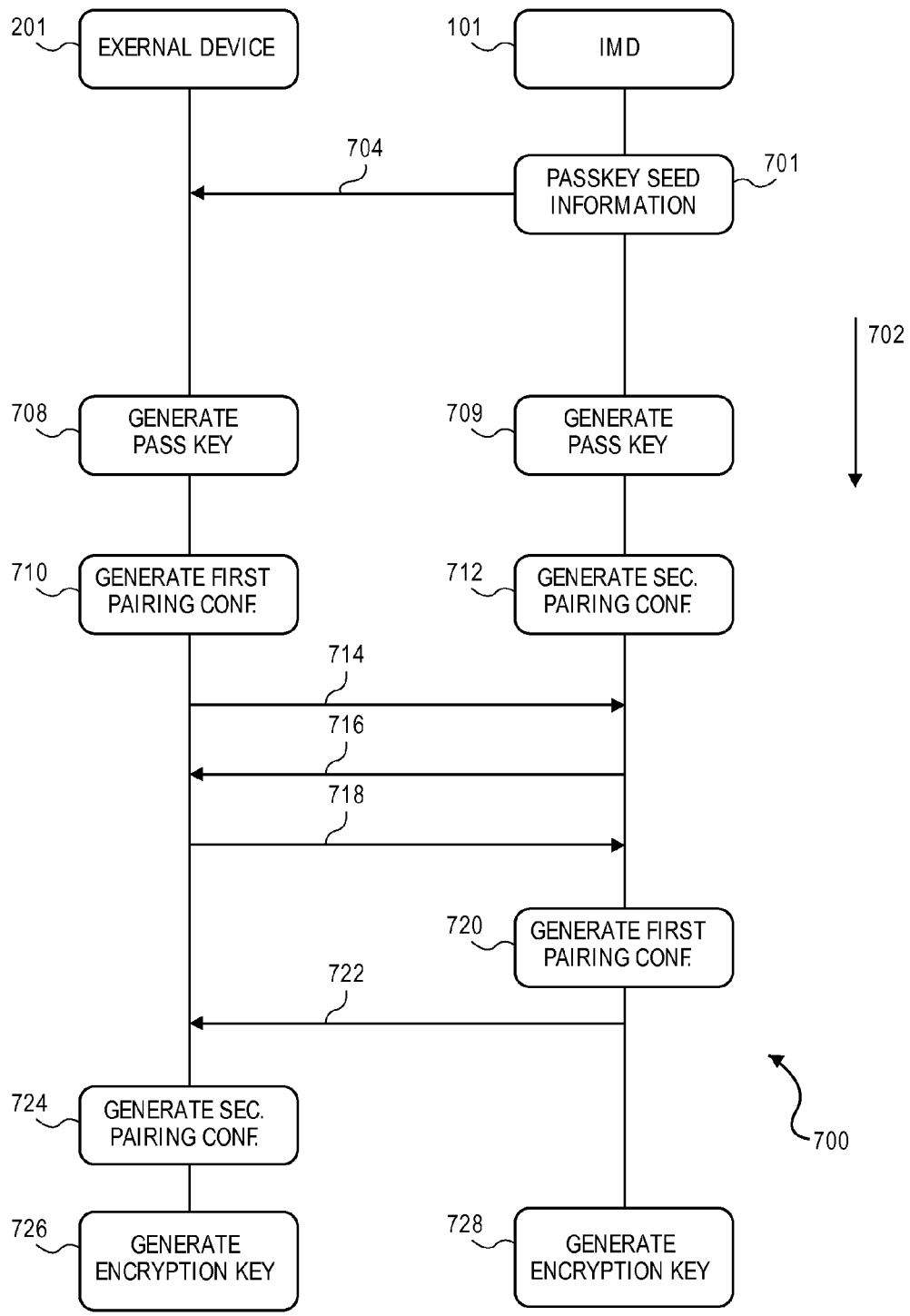
FIG. 7 illustrates a message sequence chart between an implantable medical device and an external device during a defined pairing procedure, according to an embodiment of the present disclosure.

During the select communication initialization mode corresponding to the predefined pairing and/or bonding procedure, the IMD 101 may determine when a connection request is received from external device 201 in connection with the select communication initialization mode (e.g., the predefined pairing and/or bonding procedure) by comparing the instructions (e.g., a connection request) from the payload to a stored instruction set on the memory 194 for the wireless protocol. In response to the connection request, the IMD 101 may be programmed and/or configured to transmit passkey seed information 701 to the external device 201 when the connection request is received by the IMD 101 through a dedicated advertisement channel. FIG. 7 illustrates a message sequence chart 700 between the external device 201 and the IMD 101 during a bonding procedure, in accordance with an embodiment. A vertical arrow 702 represents the progression of time. During the bonding procedure, the external device 201 and the IMD 101 generate passkeys 708 and 709.

The passkeys 708 and 709 may be based on passkey seed information 701 transmitted from the IMD 101. The passkey seed information may include a static identification of the IMD 101. The static identification may be stored on the memory 194 representing a product serial identification number of the IMD 101, which is a unique number assigned to the IMD 101 by a manufacturer of the IMD 101. Optionally, the static identification may be a pre-determined number stored on the memory 194 set by a clinician.

Additionally or alternatively, the passkey seed information 701 may include a dynamic seed and an encrypted static identification based on the dynamic seed. For example, the dynamic seed may be generated by, for example, the microcontroller 160, of the IMD 101 through a random number generator and stored on memory (e.g., the memory 194). Optionally, the dynamic seed may be generated from the local system clock of the IMD 101. Once the dynamic seed is generated, the microcontroller 160 may generate an encrypted static identification from an encryption algorithm based on the dynamic seed and the static identification. The encryption algorithm may be stored on the memory 194.

The microcontroller 160 may include the passkey information within a payload of a data packet 704 transmitted by the RF circuit 110 along the advertisement channel. The passkey seed information 701 may be received by the external device 201 through the RF circuit 354 and partitioned from the data packet 604 by the CPU 302 and/or 352 and stored on memory (e.g., ROM 304, RAM 306, memory 356, the hard drive 308). Once the passkey seed information 701 is partitioned from the data packet 704 the external device 201 may perform a decryption algorithm on the passkey seed information 701. For example, the external device 201 may perform the decryption algorithm on the encrypted static identification based on the dynamic seed included in the passkey seed information 701 The decryption algorithm allows the external device 201 to determine the static identification of the IMD 101.

Based on the passkey seed information 701 (e.g., dynamic seed, the static identification), the external device 201 and the IPG 101 may generate the passkeys 708 and 709. For example, the passkey may be generated from a pre-defined algorithm stored on the memory 194 of the IMD 101 and the memory (e.g., ROM 304, RAM 306, memory 356, the hard drive 308) of the external device 201. The CPU 302 or 352 may access the pre-defined algorithm and input the passkey information 701 to generate the passkey 708. Similarly, the microcontroller 160 may access the pre-defined algorithm and input the passkey seed information 701 to generate the passkey 709. It should be noted that the same passkey seed information 701 may be used for the external device 201 and the IMD 101 to generate the passkeys 708 and 709.

Optionally, once the passkeys 708 and 709 are generated the external device 201 and the IMD 101 may generate first and second pairing confirmation values 710 and 712. The first and second pairing confirmation values 710 and 712 may be a predetermined acknowledgement codes defined by the wireless protocol and stored on the memory (e.g., the memory 194, the memory 356, ROM 304, RAM 306, the hard drive 308) of each device 201 and 101. The first and second pairing confirmation values 710 and 712 are generated using the passkeys 708 and 709 generated by the devices 201 and 101, respectively. The first and second pairing confirmation values 710 and 712 may be transmitted by each device 201 and 101 within data packets 714 and 716, respectively. Once each of the first and second pairing confirmation values 710 and 712 are received, the devices 201 and 101 may partition and deconstruct the confirmation values 710 and 712 using the passkey 708 and 709 of the respective device 201 and 101. The deconstructed confirmation values may be compared with the predetermined acknowledgement codes on the memory of the devices 201 and 101. If the deconstructed confirmation values match the predetermined acknowledgement codes, the CPU 302 and the microcontroller 160 may determine that the generated passkeys 708 and 709 of each device 201 and 101 match and the bonding procedure may continue (e.g., generate encryption keys 726 and 728). Alternatively, if the deconstructed confirmation values do not match, the communication link 104 may be terminated by the respective device 201 and 101. It should be noted that the passkeys 708 and 709 are not transmitted between either device 201 and 101.

Additionally or alternatively, the first and second pairing confirmation values 710 and 712 may be based on a first and second test value, respectively. For example, the external device 201 generates the first pairing confirmation value 710 based on the passkey 708 and the first test value. The first test value, for example, may be a random value determined by the CPU 302. The first pairing confirmation value 710 is transmitted to the IMD 101 within a payload of a data packet 714.

Likewise, the IMD 101 generates the second pairing confirmation value 712 based on the passkey 709 and the second test value. The second test value, for example, may be a random value determined by the microcontroller 160. The second pairing confirmation value 712 is transmitted to the external device 201 within a payload of the data packet 716. Once the data packet 716 is received, the external device 201 may transmit a data packet 718 that includes the first test value used by the external device 201 to generate the first pairing confirmation value 710. The IMD 101 may attempt to re-generate the first pairing confirmation value 720 (also referred to as a third or new pairing confirmation value) using the passkey 709 and the first test value. The IMD 101 may compare the third pairing confirmation value with the first pairing confirmation value 710. If the first and third pairing confirmation values match, the microcontroller 160 may determine that the external device 201 is using the appropriate passkey and may proceed with the bonding procedure. Alternatively, if the values do not match, the IMD 101 may terminate the communication link 104.

Once the microcontroller 160 determines that the values match, the IMD 101 may transmit a data packet 722 that includes the second test value used to generate the second pairing confirmation value 712. The external device may attempt to re-generate the second pairing confirmation value at 724 (also referred to as a fourth or new pairing confirmation value) using the passkey 708 and the second test value. If the second and fourth pairing confirmation values match, the CPU 302 may determine that the IMD 101 is using the appropriate passkey and may proceed with the bonding procedure. Alternatively, if the values do not match, the external device 201 may terminate the communication link 104.

In various embodiments, optionally, the external device 201 and the IMD 101 utilize the Bluetooth Low Energy ("BLE") protocol. The BLE protocol is defined within "Bluetooth Specification Version 4.1, published Dec. 3, 2013 (incorporated herein by reference). For example, the BLE protocol includes a security manager that uses a key distribution approach to perform identity and encryption functionalities that is performed using a bonding procedure to establish an encryption key in two phases. In the first phase pairing request is transmitted by an initiator to a responder. In the second phase a short term key (STK) (e.g., encryption key) is generated. The encryption key (e.g., a short term key (STK)) is determined based on a predefined function defined within the BLE protocol that uses a 128-bit temporary key (TK) that is translated from a randomly generated six digit passkey.

For example, the pairing request may be included within the data packet 704 transmitted by the external device 201 with the passkey information 701. Optionally, the pairing request may be initiated by the external device 201 as a confirmation packet. Additionally or alternatively, the IMD 101 may transmit the pairing request within the data packet 704. The TK may be translated from the passkeys 708 and 709 generated by the external device 201 and the IMD 101, respectively, from the passkey information 701, which may also be used to generate encryption keys 726 and 728.

Once the bonding procedure 700 is complete, the communication link 104 between the external device 201 and the IMD 101 is fully formed and encrypted. Optionally, the external device 201 and the IMD 101 may generate an application encryption key to be used by user software of the external device 201. For example, the clinician may be running a program or application on the external device 201. The program initiates a security procedure, which requires verification that the external device 201 and the IMD 101 are paired correctly before the external device 201 may program or adjust/access settings of the IMD 101. The application encryption key may be generated by the external device 201 and the IMD 101 from an application encryption algorithm based on the passkey 708 and 709 generated at the respective devices, the static identification, the dynamic seed, or the like. Once the application encryption keys are generated the application on the external device 201 may encrypt data or requests based on the application encryption key. If the IMD 101 and/or external device 201 did not generate a matching passkey, the external device 201 has an incorrect static identification and/or dynamic seed the communications between the devices would not be able to correctly determine the instructions from the external device 201 resulting in the communication link 104 being terminated by the application.

Figure 8:
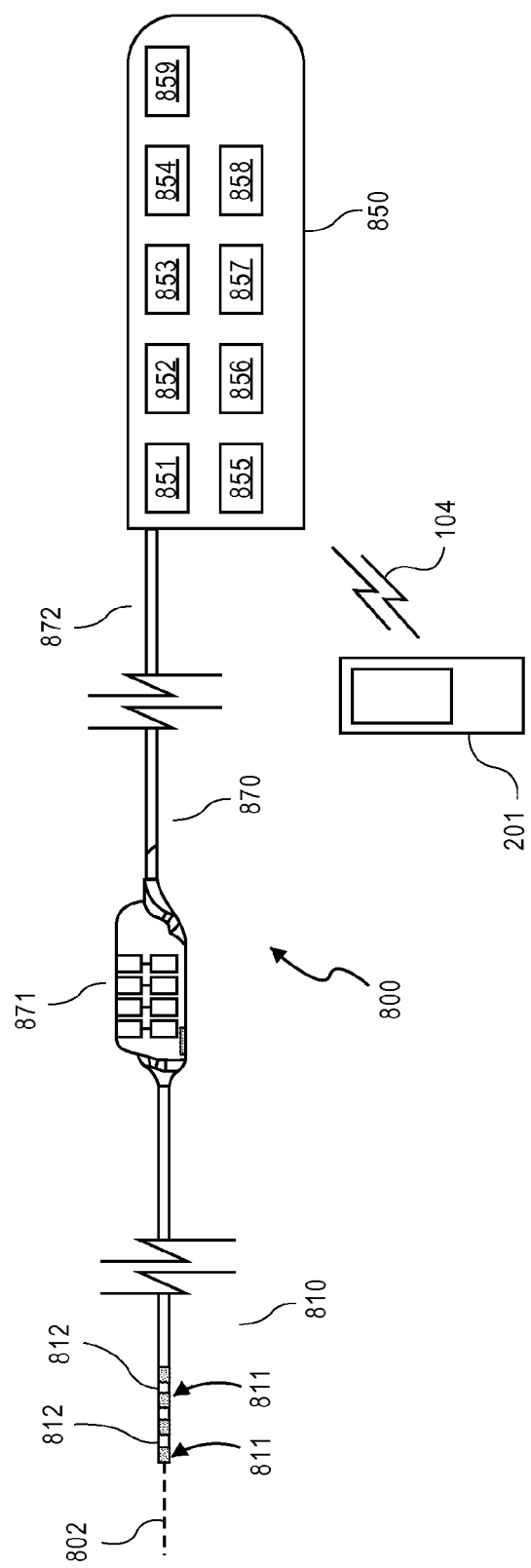
FIG. 8 illustrates a block diagram of exemplary internal components of an implantable medical device, according to an embodiment of the present disclosure.

FIG. 8 illustrates a block diagram of exemplary internal components of the IMD 800, in accordance with an embodiment. For example, the IMD 800 may be a neurostimulator adapted to stimulate spinal cord tissue, peripheral nerve tissue, deep brain tissue, cortical tissue, cardiac tissue, digestive tissue, pelvic floor tissue, or any other suitable nerve tissue of interest within a patient's body.

The IMD 800 may include an implantable pulse generator (IPG) 850 that is adapted to generate electrical pulses applied to the tissue of a patient. Additionally or alternatively, the IPG 850 may be an external neuro pulse generator. The IPG 850 typically comprises a metallic housing that encloses a controller 851, pulse generating circuitry 852, a charging coil 853, a battery 854, RF circuit 855, battery charging circuitry 856, switching circuitry 857, memory 858, a triggering circuit 859, and the like.

The controller 851 (also referred to herein as a processor module or unit) typically includes a microprocessor, or equivalent control circuitry, designed specifically for controlling the components of the IPG 800 and may further include RAM or ROM memory, logic and timing circuitry, state machine circuitry, and I/O circuitry. Typically, the controller 851 includes the ability to process or monitor input signals (data) as controlled by program code stored in memory. The details of the design and operation of the controller 851 are not critical to the invention. Rather, any suitable controller 851 may be used that carries out the functions described herein.

The IPG 850 may comprise a separate or an attached extension component 870. If the extension component 870 is a separate component, the extension component 870 may connect with a "header" portion 872 of the IPG 850 as is known in the art. If the extension component 870 is integrated with the IPG 850, internal electrical connections may be made through respective conductive components. Within the IPG 850, electrical pulses are generated by the pulse generating circuitry 852 and are provided to the switching circuitry 857. The switching circuitry 857 connects to outputs of the IPG 850. Electrical connectors (e.g., "Bal-Seal" connectors) within the connector portion 871 of the extension component 870 or within the IPG header may be employed to conduct various stimulation pulses. The terminals of one or more leads 810 are inserted within connector portion 871 or within the IPG header 872 for electrical connection with respective connectors. Thereby, the pulses originating from the IPG 850 are provided to the leads 810. The pulses are then conducted through the conductors of the lead 810 and applied to tissue of a patient via stimulation electrodes 811 that may be coupled to blocking capacitors. Any suitable known or later developed design may be employed for connector portion 871.

The stimulation electrodes 811 may be positioned along a horizontal axis 802 of the lead 810, and are angularly positioned about the horizontal axis 802 so the stimulation electrodes 811 do not overlap. The stimulation electrodes 811 may be in the shape of a ring such that each stimulation electrode 811 continuously covers the circumference of the exterior surface of the lead 810. Each of the stimulation electrodes 811 are separated by non-conducting rings 812, which electrically isolate each stimulation electrode 811 from an adjacent stimulation electrode 811. The non-conducting rings 812 may include one or more insulative materials and/or biocompatible materials to allow the lead 810 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The stimulation electrodes 811 may be configured to emit the pulses in an outward radial direction proximate to or within a stimulation target. Additionally or alternatively, the stimulation electrodes 811 may be in the shape of a split or non-continuous ring such that the pulse may be directed in an outward radial direction adjacent to the stimulation electrodes 811. Examples of a fabrication process of the stimulation electrodes 811 is disclosed in U.S. Publication No. 2011/0072657, entitled, "METHOD OF FABRICATING STIMULATION LEAD FOR APPLYING ELECTRICAL STIMULATION TO TISSUE OF A PATIENT," which is expressly incorporated herein by reference.

It should be noted the stimulation electrodes 811 may be in various other formations, for example, in a planar formation on a paddle structure as disclosed in U.S. patent application Ser. No. 14/198,260, entitled, "PADDLE LEADS FOR NEUROSTIMULATION AND METHOD OF DELIVERYING THE SAME," which is expressly incorporated herein by reference.

The lead 810 may comprise a lead body 870 of insulative material about a plurality of conductors within the material that extend from a proximal end of lead 810, proximate to the IPG 850, to its distal end. The conductors electrically couple a plurality of the stimulation electrodes 811 to a plurality of terminals (not shown) of the lead 810. The terminals are adapted to receive electrical pulses and the stimulation electrodes 811 are adapted to apply the pulses to the stimulation target of the patient. Also, sensing of physiological signals may occur through the stimulation electrodes 811, the conductors, and the terminals. It should be noted that although the lead 810 is depicted with four stimulation electrodes 811, the lead 810 may include any suitable number of stimulation electrodes 811 (e.g., less than four, more than four) as well as terminals, and internal conductors. Additionally or alternatively, various sensors (e.g., a position detector, a radiopaque fiducial) may be located near the distal end of the lead 810 and electrically coupled to terminals through conductors within the lead body 870.

For implementation of the components within the IPG 850, a processor and associated charge control circuitry for an IPG is described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 856) of an IPG 850 using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference.

An example and discussion of "constant current" pulse generating circuitry (e.g., pulse generating circuitry 852) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IPG 850. Different pulses on different stimulation electrodes 811 may be generated using a single set of the pulse generating circuitry 852 using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., tonic stimulation waveform, burst stimulation waveform) that include generated and delivered stimulation pulses through various stimulation electrodes 811 of one or more leads 810 as is also known in the art. Various sets of parameters may define the pulse characteristics and pulse timing for the pulses applied to the various stimulation electrodes 811 as is known in the art. Although constant current pulse generating circuitry is contemplated for some embodiments, any other suitable type of pulse generating circuitry may be employed such as constant voltage pulse generating circuitry.

The IPG 850 may include a trigger circuit 859 that functions in accordance with embodiments described herein. The trigger circuit 859 may include a Hall Effect sensor, MEMS sensor, an inductor, an inductive telemetry antenna, an accelerometer, an NFC receiver, and/or the like. Optionally, the trigger circuit 859 may include amplifiers, analog to digital converters, memory storage devices, digital signal processors, or the like. Additionally or alternatively, all or portions of the trigger circuit 859 may be integrated within the RF circuit 855 and/or the controller 851. The trigger circuit 859 may be monitored by the controller 851 to detect the presence of the activation field 109 generated by the triggering device 102. The trigger circuit 859 may change an electrical potential (e.g., voltage) signal to the controller 851 when a portion of the activation field 109 overlaps the IMD 800.

The stimulation parameters (e.g., amplitude, frequency, type of stimulation waveform) and other operating parameters of the IMD 800 may be non-invasively programmed into the memory 858 through the RF circuit 855 in bi-directional wireless communication link with the external device 201. For example, the external device 201 may permit the user to move electrical stimulation along and/or across one or more of the lead(s) 810 using different stimulation electrode 811 combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference. The controller 851 controls the RF circuit 855 and receives data/transmissions from the RF circuit 855. The RF circuit 855 further allows status information relating to the operation of IMD 800 (as contained in the controller 851 or memory 858) to be sent to the external device 201 through an established bi-directional communication link 104.

The controller 851 may support a particular wireless communication protocol while communicating with the external device 201, such as Bluetooth low energy, Bluetooth, ZigBee, Medical Implant Communication Service ("MICS"), or the like. Protocol firmware may be stored in memory 858, which is accessed by the controller 851. The protocol firmware provides the wireless protocol syntax for the controller 851 to assemble data packets, establish communication links 104, and partition data received from the external device 201.

The memory 858 may also contain a pre-defined algorithm that generates a passkey. The passkey may be used to initiate a bonding procedure between the IMD 800 and the external device 201 to establish a secured bi-directional communication session over the communication link 104. The passkey may be generated based on a dynamic seed and/or a static identification received by the RF circuit 855 through the communication link 104 from the external device 201 and inputted into the pre-defined algorithm. Optionally, the dynamic seed may be a random number generated by the controller 851, based on the local system clock of the IMD 800, or the like that is transmitted by the RF circuit 855 to the external device. Additionally or alternatively, the static identification may be stored on the memory 858 representing a product serial identification number of the IMD 800, which is a unique number assigned to the IMD 800 by a manufacturer of the IMD 800. Optionally, the static identification may be a pre-determined number stored on the memory 858 set by a clinician.

To establish the communication link 104 between the external device 201 and the IMD 800, the controller 851 instructs the RF circuit 855 to transmit an advertisement notice on an advertisement channel. The advertisement channel is a point to multipoint, unidirectional, channel to carry a repeating pattern of system information messages such as network identification, allowable RF channels to establish the communication link 104, and the like that is included within the advertisement notice. The advertisement notice may be repeatedly transmitted after a set duration or an advertisement period until the IMD 800 receives a connection request from the external device 201 to form a communication link 104 and transmit within a data channel of the wireless protocol.

The length of the advertisement period may be adjusted by the controller 851 when entering an advertisement mode. During the advertisement mode, the controller 851 may reduce the length of the advertisement period relative to not being in the advertisement mode. The reduced length of the advertisement period results in the RF circuit 855 transmitting more or an increased number of advertisement notices relative to not being in the advertisement mode. The controller 851 may enter the advertisement mode after detecting a predetermined signal directed at the IMD 800.

The controller 851, the microcontroller 160, and CPUs 302 and 352 may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the controller 851, the microcontroller 160, and CPUs 302 and 352 represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The controller 851, the microcontroller 160, and CPUs 302 and 352 may execute a set of instructions that are stored in one or more storage elements, in order to process data. The storage elements may also store data or other information as desired or needed. The storage element may be in the form of an information source or a physical memory element within the controller 851, the microcontroller 160, and CPUs 302 and 352. The set of instructions may include various commands that instruct the controller 851, the microcontroller 160, and CPUs 302 and 352 to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be construed with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112(f), unless and until such claim limitations expressly use the phrase "means for" followed by a statement of function void of further structure.

What is claimed is:

1. A method for initiating a bi-directional communication link, the method comprising:
configuring an implantable medical device (IMD) to detect an activation field from a triggering device when the triggering device is positioned proximate to the IMD, and to identify a field characterization of the activation field;
configuring the IMD to establish a bi-directional communication link with an external device through a select communication initialization mode from a plurality of communication initialization modes defined by a wireless protocol in response to the field characterization of the activation field.

2. The method of claim 1, wherein the select communication initialization mode corresponds to a defined pairing procedure.

3. The method of claim 1, further comprising programming the IMD to activate a radio frequency circuit when the activation field is detected.

4. The method of claim 1, further comprising programming the IMD to periodically transmit an advertisement notice through a dedicated advertisement channel in connection with the select communication initialization mode for a predetermined time.

5. The method of claim 1, further comprising programming the IMD to:
determine when a connection request is received from the external device in connection with the select communication initialization mode, wherein the connection request corresponds to a predefined pairing procedure; and
transmit passkey seed information to the external device when the connection request is received by the IMD.

6. The method of claim 5, further comprising programming the IMD to at least one of disable a radio frequency circuit or end the select communication initialization mode when a connection request is not received within a predetermined period.

7. The method of claim 5, wherein the passkey seed information comprises at least one of a static identification of the IMD or a dynamic seed generated by the IMD.

8. The method of claim 1, wherein the activation field from the triggering device comprises at least one of a magnetic field, a near field communication transmission, a radio frequency identification signal, an inductive telemetry signal, or a vibration scheme.

9. The method of claim 1, wherein the triggering device comprises at least one of a magnet, inductive coil circuitry, a near field communication circuit, or an electric motor.

10. The method of claim 1, wherein the wireless protocol constitutes at least one of a Bluetooth protocol, a Bluetooth low energy protocol, or a ZigBee protocol.

11. A system for initiating a bi-directional communication link comprising:
an external device;
a triggering device; and an implantable medical device (IMD) comprising a trigger circuit, wherein the trigger circuit is configured to detect an activation field from the triggering device when the triggering device is positioned proximate to the IMD, the IMD further configured to identify a field characterization of the activation field and establish a bi-directional communication link with an external device through a select communication initialization mode from a plurality of communication initialization modes defined by a wireless protocol in response to the field characterization of the activation field.

12. The system of claim 11, wherein the select communication initialization mode corresponds to a defined pairing procedure.

13. The system of claim 11, wherein the IMD is further configured to activate a radio frequency circuit when the activation field is detected.

14. The system of claim 11, wherein the IMD is further configured to periodically transmit an advertisement notice through a dedicated advertisement channel in connection with the select communication initialization mode for a predetermined time.

15. The system of claim 11, wherein the IMD is further configured to:

determine when a connection request is received from the external device in connection with the select communication initialization mode, wherein the connection request corresponds to a predefined pairing procedure; and transmit passkey seed information to the external device when the connection request is received by the IMD.

16. The system of claim 15, wherein the IMD is further configured to at least one of disable radio frequency circuit of the IMD or end the select communication initialization mode when a connection request is not received within a predetermined period.

17. The system of claim 15, wherein the passkey seed information comprises at least one of a static identification of the IMD or a dynamic seed generated by the IMD.

18. The system of claim 11, wherein the activation fields from the triggering device comprises at least one of a magnetic field, a near field communication transmission, a radio frequency identification signal, inductive coil circuitry, communication transmission, or a vibration scheme.

19. The system of claim 11, wherein the triggering device comprises at least one of a magnet, an inductive communication circuit, a near field communication circuit, or an electric motor.

20. The system of claim 11, wherein the wireless protocol constitutes at least one of a Bluetooth protocol, a Bluetooth low energy protocol, or a ZigBee protocol.

* * * * *